United States Patent [19]
Horwitz et al.

[11] Patent Number: 5,854,968
[45] Date of Patent: Dec. 29, 1998

[54] PROCESS AND APPARATUS FOR THE PRODUCTION OF BI-213 CATIONS

[75] Inventors: E. Philip Horwitz, Naperville; John J. Hines, Newark; Renato Chiarizia; Mark Dietz, both of Elmhurst, all of Ill.

[73] Assignee: Arch Development Corporation, Chicago, Ill.

[21] Appl. No.: 871,517

[22] Filed: Jun. 9, 1997

[51] Int. Cl.⁶ .................................................. C01G 29/00
[52] U.S. Cl. ................................. 423/2; 423/6; 423/249; 250/432 PD; 210/682
[58] Field of Search ............. 923/2.6, 249; 250/432 PD; 424/1.49; 210/682

[56] References Cited

U.S. PATENT DOCUMENTS

| | | |
|---|---|---|
| 2,873,170 | 2/1959 | Hyde et al. . |
| 4,665,129 | 5/1987 | Atcher et al. ................................ 423/2 |
| 5,256,808 | 10/1993 | Alexandratos ........................... 558/142 |
| 5,281,631 | 1/1994 | Horwitz et al. ............................ 521/38 |
| 5,355,394 | 10/1994 | van Geel et al. ....................... 376/189 |
| 5,449,462 | 9/1995 | Horwitz et al. ......................... 210/682 |
| 5,539,003 | 7/1996 | Horwitz et al. ............................ 521/33 |
| 5,641,471 | 6/1997 | Geerlings ................................ 424/1.49 |
| 5,651,883 | 7/1997 | Horwitz et al. ........................ 210/198.2 |

OTHER PUBLICATIONS

Young et al., *N. Engl. J. Med.*, 322, (1991) 1021.
Horwitz, E. P. et al., *Analytica Chemica Acta* 310 (1995) 63–78.
Sundell et al., *Chem. Mater.*, 5:372–376 (1993).
Sundell et al, *Polym. Prep.*, 33:992–993 (1992).
A. Suzuki et al., "Solution Chemistry of Light Actinide Elements," Japan–US. Seminar on Thorium Fuel Reactors—Proceedings, Nara, Japan, 18–22 Oct., 1982 (Tokyo, 1985) pp. 137–143.

*Primary Examiner*—Ngoclan Mai
*Attorney, Agent, or Firm*—Welsh & Katz, Ltd.

[57] ABSTRACT

A process for producing substantially impurity-free Bi-213 cations is disclosed. An aqueous acid feed solution containing Ac-225 cations is contacted with an ion exchange medium to bind the Ac-225 cations and form an Ac-225-laden ion exchange medium. The bound Ac-225 incubates on the ion exchange medium to form Bi-213 cations by radioactive decay. The Bi-213 cations are then recovered from the Ac-225-laden ion exchange medium to form a substantially impurity-free aqueous Bi-213 cation acid solution. An apparatus for carrying out this process is also disclosed.

14 Claims, 6 Drawing Sheets

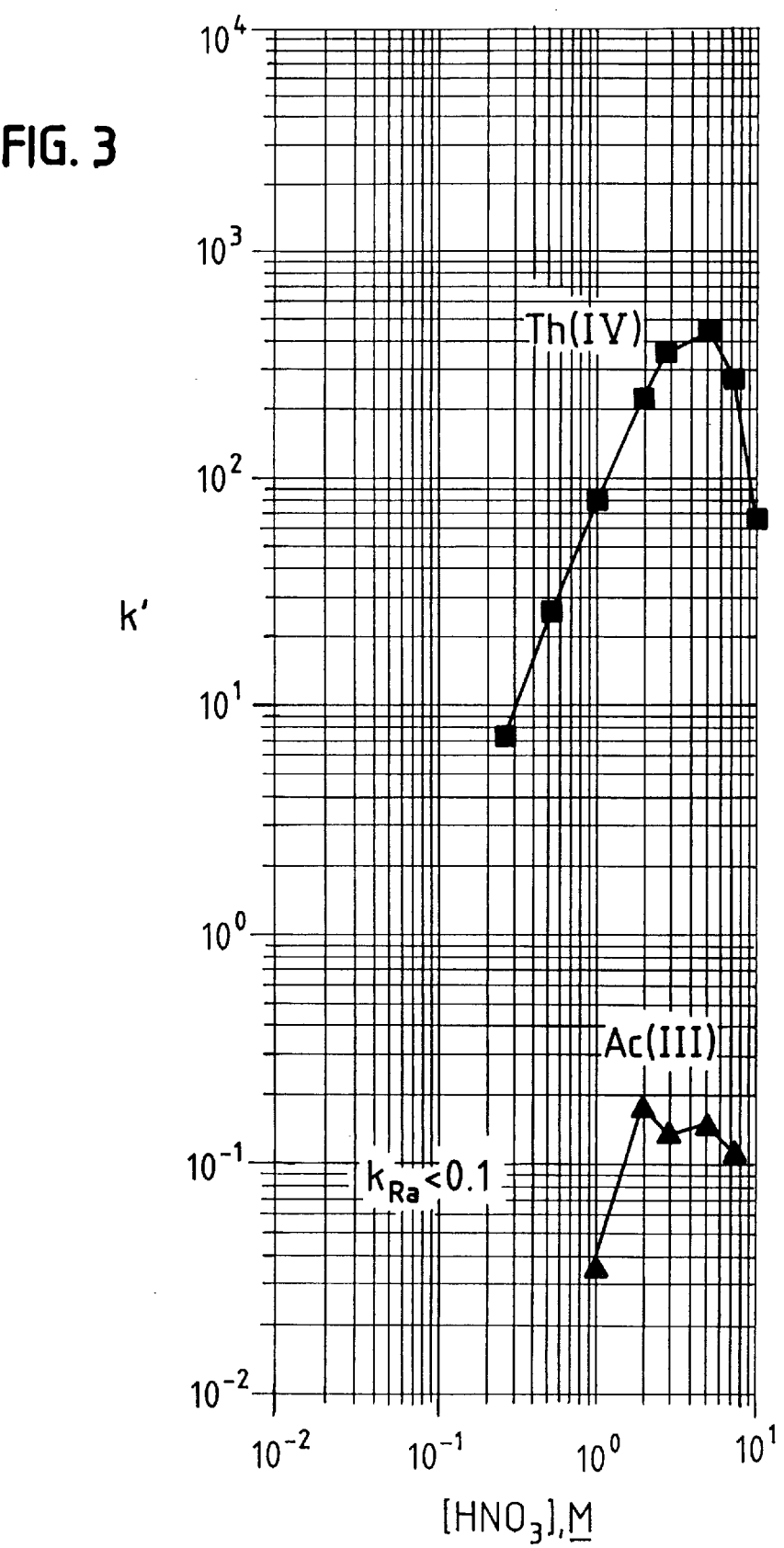

PROCESS AND APPARATUS FOR THE PRODUCTION OF BI-213 CATIONS

GOVERNMENTAL RIGHTS

This invention was made with governmental support pursuant to Contract No.W-31-109-ENG-38 between the U.S. Department of Energy and The University of Chicago, contractor for Argonne National Laboratory. The Government has certain rights in this invention.

FIELD OF THE INVENTION

This invention relates to a process and apparatus for the production of bismuth-213 cations. More particularly, the invention relates to a process and apparatus for the production of substantially impurity-free bismuth-213 cations from a starting material containing actinium-225 cations.

BACKGROUND OF THE INVENTION

Ovarian carcinoma has the highest mortality rate of any gynecologic cancer. This is due, in part, to the usually observed late detection of the disease and the consequent spread of the disease outside of the pelvis by the time the disease is diagnosed. Cytoreductive surgery and therapy have improved the overall survival rate, however, relapses have been observed even after apparent complete remission.

Initial treatment of stages III and IV ovarian carcinoma with multiple chemotherapy agents yields responses of about 90 percent. However, after four years, only about 30 percent of the patients are expected to survive. Current treatment strategies following relapse include intraperitoneal chemotherapy and abdominopelvic external beam therapy. These treatments, however, have been shown to be largely ineffective.

Radiation therapy, such as X-ray therapy, has been observed to be the most effective treatment for microscopic disease. Microscopic disease refers to the layers of diseased cells remaining after removal of a tumor, cells of a tumor that are beginning to form and the first few cell layers of tumor growth and formation. The use of radiation therapy is limited by the radio tolerance of normal cells and by technical problems encountered in delivering tumoricidal doses.

In addition, it is believed that the lack of response to conventional radiation therapy may be due, in part, to the quality of radiation that is used. For example, X-ray therapy is low-LET (linear energy transfer), is sparsely ionizing and its effectiveness is dependent on cellular oxygen.

Radionuclide therapy using chromatic phosphate (P-32), which is a beta-emitter, has exhibited some level of success. It has been reported that a five-year survival rate of 81 percent for the treatment of microscopic disease has been shown in Stage I and Stage II disease. Young et al. *N.Engl. J.Med.* 322 (1991) 1021. Nevertheless, like X-ray therapy, P-32 is low-LET, is sparsely ionizing and its effectiveness is also dependent on cellular oxygen.

Alpha-emitting radionuclides have also been found to be effective in the treatment and eradication of microscopic carcinoma. This is believed to be a result of the densely ionizing radiation that is emitted during decay, and the cellular oxygen independence of the effect of the alpha particle on the disease.

It has been shown that lead-212 (Pb-212) and astatine-211 (At-211) are effective in the treatment and eradication of microscopic carcinoma. However, known methods for producing such alpha particle emitting nuclides are limited in that they generally require the use of particle accelerators for their production. Moreover, the radionuclides are often contaminated with impurities, both chemical and radiochemical, that are difficult to filter out or otherwise remove from the desired nuclide. It has also been found that such nuclides contaminated with impurities do not have the desired property of even distribution to the affected area after intraperitoneal administration.

Bismuth-212, which is an alpha-emitting radionuclide, has also recently been found to exhibit the desirable properties associated with Pb-212 and At-211, in that it provides highly ionizing radiation and its effects are independent of cellular oxygen. Moreover, certain formulations of Bi-212 have also been found to overcome the distributional problems encountered with Pb-212 and At-211 upon intraperitoneal administration.

Although Bi-212 has been found to be a successful candidate for radiotherapy treatment of microscopic carcinoma, its production is complicated by the fact that radon-220 (Rn-220), is one of the decay products in the radioactive decay chain leading to Bi-212. Rn-220 is a gaseous radioisotope that can be difficult to manage, e.g., contain and process.

Another disadvantage in the use of Bi-212 is that one of its decay products is thallium-208 (Tl-208). As Tl-208 decays to stable lead-208, it emits an undesirable, high energy; i.e., 2.6 Mev, gamma ray.

Bi-213, which is also an alpha-emitting bismuth isotope, has been found to exhibit the beneficial properties of Bi-212, without the undesirable production of gaseous Rn-220, and without the undesirable production of the gamma-emitting Tl-208. Moreover, Bi-213 has a half-life of about 45.6 minutes and ultimately decays to stable Bi-209, which makes it an ideal candidate for intraperitoneal treatment.

Moreover, because of the highly ionizing nature of the radioisotopes, and in particular, the alpha-emitting isotopes, and because of the substantially short half-life of Bi-213, it would be most desirable to produce Bi-213 at a location remote from a particle accelerator or other source, and as physically close to the patient as possible. It would, of course, be most beneficial to produce the isotope at the patient's "bed-side" to reduce the stress on the patient and reduce or eliminate the need for specifically designed facilities for radiotherapy.

Accordingly, there continues to be a need for a method and apparatus for the production of substantially impurity-free Bi-213. Such a method and apparatus should permit production of Bi-213 at a location remote from an associated particle accelerator or other source such as the decay of U-233. Such a method and apparatus should further permit production of Bi-213 without the generation of undesirable radioactive gases, such as radon. Such an apparatus should additionally be sufficiently portable so that it can be transported to a patient for administration and treatment without special facilities. The disclosure that follows provides one such apparatus and a process for its use.

SUMMARY OF THE INVENTION

A process for producing substantially impurity-free Bi-213 is contemplated. In practical application, Bi-213 is obtained from an aqueous feed solution that is produced from the decay products of uranium-233 (U-233). During the production of U-233, other isotopic forms of uranium, such as U-232 as well as decay products (e.g., daughter, grand-daughter, great-grand daughter, collectively referred to simply as decay products) of the uranium isotopes are produced. In order to produce Bi-213 that is substantially free of impurities; i.e., free of impurities other than decay products of Bi-213 itself, the U-233 decay product actinium-225 (Ac-225) is isolated from all of the other decay products of U-233 as well as all of the decay products of U-232. The Ac-225 that is isolated from all of the other isotopes is maintained for a predetermined period of time to produce Bi-213 that is substantially free of impurities by radioactive decay.

The Ac-225 is isolated from the other isotopes by contacting the aqueous feed solution with a first exchange medium to remove isotopic cations having a higher valency than Ac-225 (such as thorium-228 and -229 whose valencies are +4), then contacting the thorium-depleted solution with a subsequent, second exchange medium to bind substantially only the Ac-225 thereto. The Ac-225 has the next lower valency; i.e., +3. The other, lower valency isotopic cations (+2 and lower) are passed through during the subsequent exchange medium contact.

The process comprises the steps of contacting an aqueous nitric acid feed solution having actinium-225 (Ac-225) with an exchange medium having a plurality of binding sites adapted to bind the Ac-225 thereto to form an Ac-225-laden ion exchange medium. The Ac-225-laden ion exchange medium is incubated (maintained) for a predetermined period of time to form Bi-213 from Ac-225 by radioactive decay.

An aqueous acid solution, preferably hydrochloric acid, is contacted with the Ac-225-laden ion exchange medium to release the formed Bi-213 therefrom and form a Bi-213-containing acid solution. The Bi-213-containing acid solution is recovered from the Ac-225-laden ion exchange medium typically by elution to form a substantially impurity-free acid solution of Bi-213 cations. The Bi-213 acid solution can be subsequently neutralized and diluted to form an isotonic solution for patient administration.

In a preferred process, the aqueous feed solution that is obtained from U-233 includes some U-232, cations of thorium (thorium-228 and thorium-229) and radium (radium-224 and radium-225), as well as Ac-225 cations. The feed solution is first contacted with a first exchange medium having a plurality of binding sites thereon adapted to bind the thorium cations to form a thorium-laden exchange medium, and to remove the thorium from the feed solution to form a radium/actinium solution (the "Ra/Ac solution") that is free of cations of thorium isotopes. The actinium in the Ra/Ac solution is in the isotopic form Ac-225 because U-232 does not form an actinium daughter.

The thorium-laden exchange medium is preferably rinsed with an aqueous acid solution to further remove any residual radium and Ac-225 therefrom. The rinse solution is combined with the Ra/Ac solution to form a combined Ra/Ac solution.

The combined Ra/Ac solution is contacted with the second ion exchange medium to bind the Ac-225 thereto (and not bind the radium isotope cations), to form the Ac-225-laden ion exchange medium and a lessened amount of Ac-225 relative to the radium in the combined Ra/Ac solution.

The Ac-225-laden ion exchange medium is then incubated (maintained) for a predetermined period of time to form Bi-213 cations from Ac-225 by radioactive decay. A solution of Bi-213 cations that is free of other decay products of U-233 and -232 except its own decay products is obtained as discussed before, and is referred to herein as being substantially impurity-free.

In a contemplated process, the aqueous acidic feed solution containing thorium, radium and Ac-225 has nitric acid in a concentration of about 1 to about 10M, and preferably about 2.0M to about 3.0M, and the thorium-laden exchange medium is rinsed with an aqueous nitric acid solution having a concentration of about 1 to about 10M, and preferably about 2.0M to about 3.0M.

The combined Ra/Ac solution can, prior to contact with the ion exchange medium, be fed through a filter, such as an in-line filter, to remove particulate matter from the fluid stream. The in-line filter can include a second exchange medium to capture any thorium that may have carried over or broken through from the thorium-laden exchange medium.

The substantially impurity-free Bi-213 aqueous acid solution can also be fed through a filter having a second ion exchange medium to capture Ac-225 that may have carried over or broken through from the Ac-225-laden ion exchange medium, prior to preparation for patient administration.

Advantageously, the exchange medium that forms the thorium-laden exchange medium can be regenerated to remove the thorium isotopes therefrom by contacting the resin with about 0.01 to about 10M aqueous hydrochloric acid, and preferably about 1.0M HCl, followed by an aqueous nitric acid rinse. The resulting thorium fraction removed from the exchange medium can be evaporated and reused to further produce Ac-225, and that Ac-225 can subsequently be used to form additional Bi-213.

An apparatus for producing substantially impurity-free Bi-213 from a starting material that can include isotopes of thorium and radium, as well as Ac-225, comprises a first exchange medium contained within a first vessel. The first exchange medium has a plurality of binding sites thereon having an affinity for binding cations of isotopes of thorium thereto and having a lower affinity for binding cations of isotopes of radium and Ac-225 cations thereto. A first acid supply is in flow communication with the vessel and is adapted to supply a first acid to carry the starting material to the exchange medium in the vessel. The first vessel is adapted to retain the exchange medium in contact with the acid.

A second vessel is in flow communication with the first vessel and is adapted to retain therein a second ion exchange medium having a plurality of binding sites thereon. The second ion exchange medium binding sites have an affinity for binding Ac-225 cations thereto and have a lower affinity for binding cations of isotopes of radium thereto. A second acid supply is in flow communication with the second vessel and is adapted to supply an acid thereto. The second vessel is separable from the first vessel and the other components of the apparatus for use locally at, for example, a patient's bed-side.

A third acid supply is provided in flow communication with the second vessel for eluting the Bi-213 therefrom.

Optionally, the apparatus can include one or more in-line filters positioned, for example, between the first and second vessels and after the second vessel prior to preparation for patient administration. The filters can be provided with ion-exchange media. Other features and advantages of the present invention will be apparent from the following detailed description, the accompanying drawings, and the appended claims.

BRIEF DESCRIPTION OF THE FIGURES

In the figures forming a portion of this disclosure,

FIG. 3 is a graphic illustration of the uptake of thorium IV (squares) and actinium III (triangles) cations by a tetravalent actinide (TEVA™) exchange medium resin measured as the number of free column volumes to peak maximum (K') relative to the concentration of the nitric acid carrier solution; the uptake of radium II cations is less than 0.1 under the conditions studied;

DETAILED DESCRIPTION OF THE PREFERRED EMBODIMENTS

Figure 1:
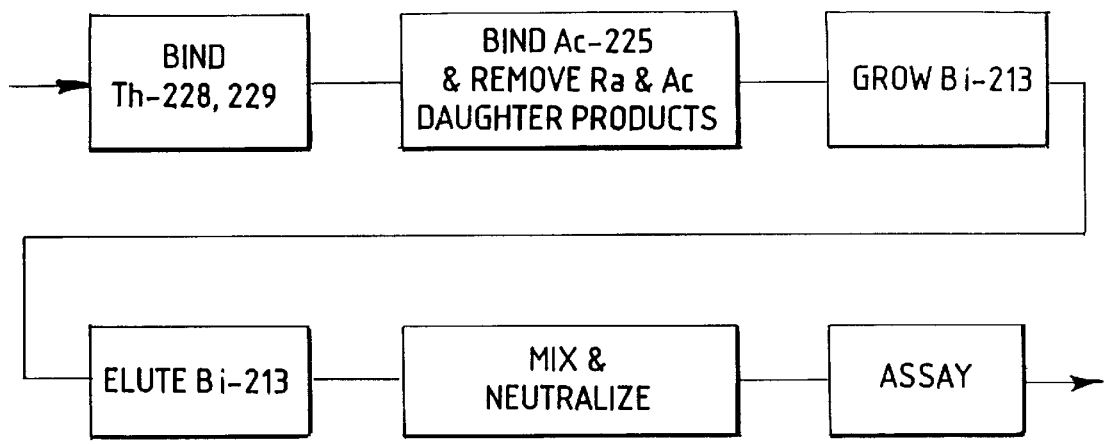
FIG. 1 is a simplified flow diagram of a process for the production of substantially impurity-free Bi-213, embodying the principles of the present invention.

Although the present invention is susceptible of embodiment in various forms, there is shown in the drawings and will hereinafter be described a presently preferred process and a presently preferred embodiment of an apparatus with the understanding that the present disclosure is to be considered an exemplification of the invention and is not intended to limit the invention to the specific process and apparatus illustrated.

Referring now to the figures, and particularly to FIG. 1, there is shown a simplified flow diagram depicting a process for producing substantially impurity-free Bi-213. The process contemplates contacting a nitric acid feed solution with an ion exchange medium, also referred to more simply as an exchange medium, having a plurality of binding sites thereon adapted to bind the Ac-225 thereto and form an Ac-225-laden ion exchange medium.

The Ac-225-laden ion exchange medium is incubated (maintained) for a predetermined period of time so as to form Bi-213 cations from Ac-225 cations by radioactive decay. An aqueous acid solution, preferably aqueous hydrochloric acid, is introduced to the Ac-225-laden ion exchange medium to release the Bi-213 cations therefrom and form a Bi-213 acid solution. The Bi-213 acid solution is recovered from the Ac-225-laden ion exchange medium to form a substantially impurity-free aqueous Bi-213 acid solution.

Figure 2A:
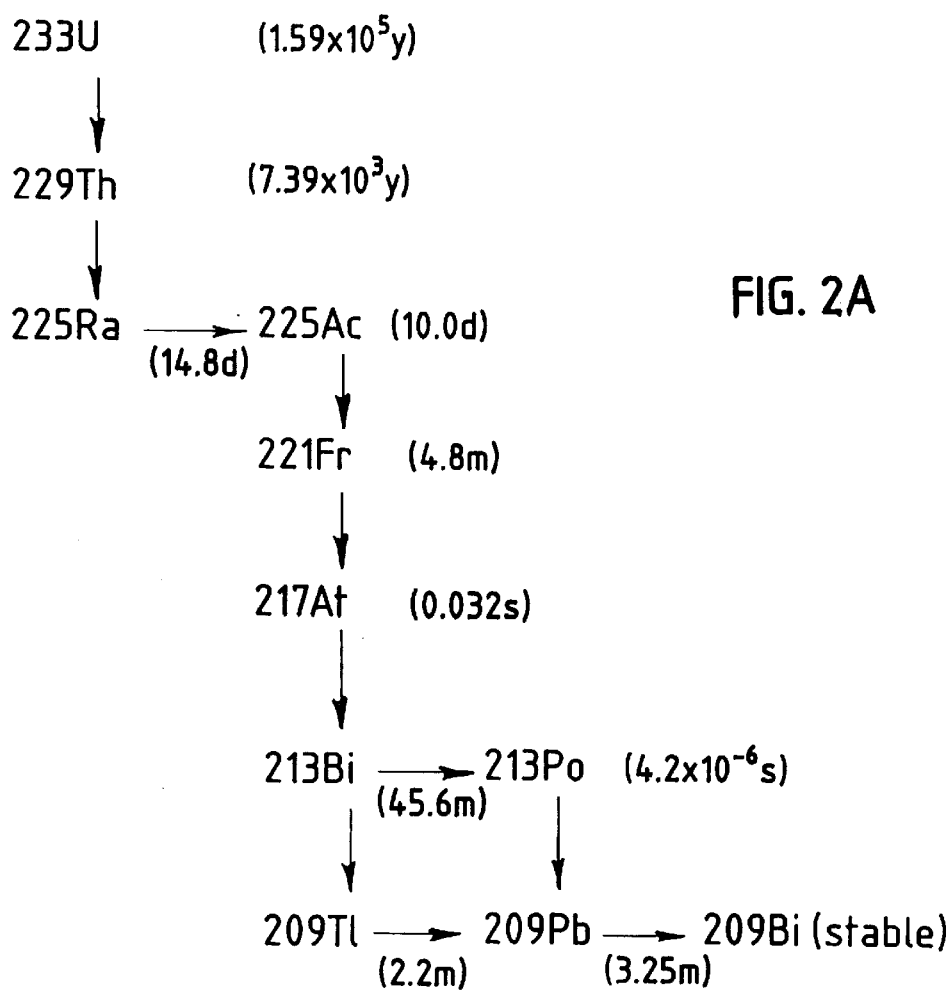
FIG. 2A is a graphic illustration of the uranium-233 (U-233) decay chain showing the decay products thereof including thorium-229 (Th-229), radium-225 (Ra-225), actinium-225 (Ac-225) and bismuth-213 (Bi-213), and in which half-lives are parenthesized in which y=years; d=days; m=minutes; and s=seconds.

In practical application, in a current process, the Bi-213 is produced from a starting material of Th-229, which is obtained from U-233. Advantageously, large quantities of U-233 were produced by, or on behalf of, the Atomic Energy Commission (now the Department of Energy) as an alternative fissile isotope for nuclear energy production. Thus, there is a large supply of U-233 for producing Th-229 and subsequently Bi-213. FIG. 2A illustrates, in part, the decay scheme of U-233, a decay product of which is the isotope Bi-213.

Figure 2B:
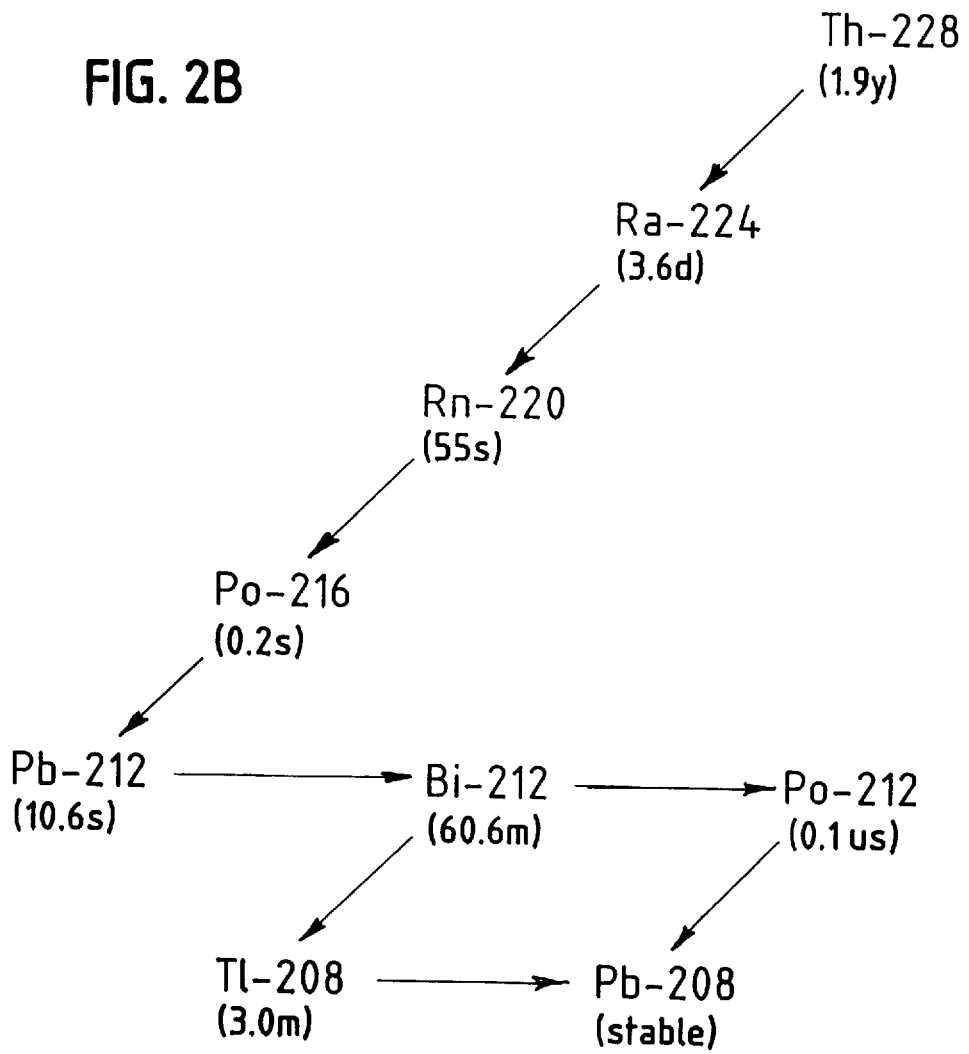
FIG. 2B is a graphic illustration of the thorium-228 (Th-228) decay chain showing the decay products thereof including radium-224 (Ra-224), radon-220 (Rn-220) and bismuth-212 (Bi-212), and in which half-lives are parenthesized in which y=years; d=days; m=minutes; and s=seconds.

The U-233, however can include various other radio-isotopes that are, for the purposes of the present process, contaminants. One of the contaminants is U-232, which decays to bismuth-212 (Bi-212). Although Bi-212 has been found to be effective in the treatment of ovarian carcinoma, one of the decay products in the U-232 chain, as shown in FIG. 2B, is gaseous radon-220 (Rn-220). Because Rn-220 is a gas, it is difficult to contain and manage.

Referring to FIGS. 2A and 2B, it is readily apparent that the decay products of U-232 are somewhat similar to those of U-233. That is, U-233 (from which Bi-213, the presently desired end product, is produced) decays through, among others, thorium-229 (Th-229), radium-225 (Ra-225) and actinium-225 (Ac-225). On the other hand, U-232 (from which Bi-212 is produced) decays through, among others, thorium-228 (Th-228), radium-224 (Ra-224) and radon-220 (Rn-220). The latter decay chain; i.e., that includes Rn-220, is to be avoided to prevent production of the radioactive gas Rn-220. Nevertheless, the two decay chains have in common thorium and radium decay products.

The current process contemplates first removing the isotopic thorium cations (Th-228 and Th-229) by contacting the aqueous nitric acid feed solution (which contains thorium, radium, actinium and actinium decay products) with a first exchange medium. The first exchange medium has a plurality of binding sites thereon adapted to bind the Th-228 and Th-229 cations thereto and form a thorium-laden exchange medium, and to remove the thorium cations from the feed solution. An aqueous Ra/Ac solution is formed from the solution removed from the thorium-laden ion-exchange medium.

The aqueous Ra/Ac solution is contacted with a second exchange medium having a plurality of binding sites thereon adapted to bind the Ac-225 cations thereto and form the Ac-225-laden ion exchange medium, and to form a solution having the radium and actinium decay product cations.

The Ac-225-laden ion exchange medium is incubated (maintained) for a predetermined period of time to form Bi-213 cations from Ac-225 by radioactive decay. An acid solution is introduced to the Ac-225-laden ion exchange medium to release the Bi-213 cations therefrom and form the Bi-213 acid solution. The aqueous Bi-213 acid solution is recovered as by elution or decantation from the Ac-225-laden ion exchange medium to form the substantially impurity-free aqueous Bi-213 cation acid solution.

Essentially, the process contemplates seratim contact of an aqueous acidic solution containing isotopic cations of thorium, radium, actinium and actinium decay products, with a first exchange medium to remove the thorium (+4 valency) cations from the acidic solution. The eluate so produced is then contacted with a second exchange medium to bind substantially only the actinium (+3 valency) cations thereto. The lower valency cations of radium and other, undesirable decay products, do not bind to the exchange medium and thus remain in solution.

The Bi-213 aqueous acid solution produced by the present process is substantially free of cationic impurities that may have been present in the starting material or that may be produced from the starting material. The Bi-213 aqueous acid solution is also free of radioactive impurities or contaminants such as decay products of Th-228 and Th-229 other than Bi-213.

The actinium is maintained for a predetermined period of time to permit the actinium to form Bi-213 cations by radioactive decay. The seriatim contact of the solution with the exchange media selectively removes the undesired radionuclides to retain only the actinium in the process for producing Bi-213 cations.

The Bi-213 aqueous acid solution produced by the present process is substantially free of chemical impurities, such as cations (other than Bi-213 cations and decay products) and anions, as well as other chemical impurities that may be present in the starting material or that may be produced from the starting material. The Bi-213 aqueous acid solution is also free of radioactive impurities or contaminants other than those of Bi-213 such as decay products of Th-228 and Th-229.

An apparatus for carrying out the process includes a first exchange medium that is a solid, stationary phase having a plurality of binding sites thereon that have an affinity for binding thorium cations thereto and having a lower affinity for binding radium cations and Ac-225 cations. The first exchange medium is retained or loaded into a vessel, such as a column. A first aqueous acid supply is in flow communication with the first exchange medium in the column, and is adapted to supply a first aqueous acid as a mobile phase to carry the starting material to the column containing the exchange medium. The column is adapted to maintain contact between the exchange medium and the acid.

A second vessel is in flow communication with the first vessel and is adapted to retain therein a second ion exchange medium having a plurality of binding sites thereon. The second ion exchange medium has a substantially high affinity for binding cations of Ac-225 thereto and has a lower affinity for binding radium cations thereto. A second aqueous acid supply is in flow communication with the second vessel and is adapted to supply an acid thereto. The second vessel is fully separable from the first vessel and the other components of the system to facilitate local production (i.e., elution) of Bi-213 cations and to enhance ready administration of the Bi-213 cations. A third aqueous acid supply is in flow communication with the second vessel to elute the Bi-213 cations therefrom. When thorium cations are not present, only this second vessel need be used.

In the present process, as illustrated schematically in FIG. 1, a first aqueous acid solution is introduced to the starting material to form an acidic solution. Due to the nature of U-233, as discussed above, the starting material can include thorium isotopes including Th-228 and Th-229, radium isotopes including Ra-224 and Ra-225, and actinium-225 (Ac-225) cations, as well as various decay products thereof and associated anions that form water-soluble salts with the cations such as chloride and nitrate. The acidic solution is contacted with a first exchange medium having a plurality of binding sites thereon that are adapted to bind Th-228 and Th-229 cations and not bind cations of lower valency to form a thorium-laden exchange medium. The solution removed from the exchange medium so formed is essentially free of Th-228 and Th-229 and forms an aqueous Ra/Ac solution.

In a preferred process, the first acid solution that is introduced to the feed material, and that forms part of the acidic solution is about 1 to about 10M nitric acid, preferably in a concentration of about 2.0M to about 3.0M. The thorium-laden exchange medium can be further rinsed with additional quantities of the nitric acid solution to remove or recover, to the maximum extent possible, the residual radium and actinium isotopes. The subsequent acid rinse solution can be combined with the Ra/Ac solution to form a combined aqueous Ra/Ac solution.

As is readily apparent, the exchange medium serves to retain ions of Th-228 and Th-229, and to permit passage of ions of Ra-224, Ra-225 and their decay products. In a present process, the first exchange medium is a tetravalent actinide (TEVA™) resin, having a quaternary ammonium salt, specifically, a mixture of trioctyl and tridecyl methyl ammonium chlorides, sorbed on a water-insoluble support that is inert to the components of the exchange composition, as is discussed in E. P. Horwitz et al. *Analytica Chemica Acta* 310 (1995) 63–78.

The TEVA™ resin is highly selective for ions having the highest valency, in the present process, Th-228 and Th-229 (whose valency are +4), relative to their decay products (whose valencies are +3 and lower). FIG. 3 shows the relative uptake of selected cations of thorium, radium and actinium by the TEVA™ resin at varying concentrations of nitric acid. As is readily apparent from viewing FIG. 3, the +4 valent thorium ions are bound to the TEVA™ resin, whereas the actinium and radium ions (whose valencies are +3 and +2, respectively) are essentially, substantially unaffected by contact with the resin under the conditions shown. The TEVA™ resin is commercially available from Eichrom Industries, Inc., located at 8205 S. Cass Avenue, Darien, Ill. U.S.A.

The combined aqueous Ra/Ac solution is then contacted with a second exchange medium, an ion exchange medium, having a plurality of binding sites thereon adapted to bind ions having the next lower valency, which, in the present process are Ac-225 cations, to form an Ac-225-laden ion exchange medium. The ion exchange medium (second exchange medium) serves to retain the Ac-225 (+3 valency) bound thereto and to pass through the radium isotopes (+2 valency) and any cations of +1 valency such as sodium, potassium ions or a proton, as well as anions and any non-actinium decay products of radium and decay products formed from the decay of actinium isotopes, such a francium-221 (+1 valency) and astatine-217 (−1 valency). The material thus remaining bound to the ion exchange medium is essentially only Ac-225 because the binding sites thereon bind the +3 valent Ac-225 cations in preference to cations of lower valency and anions.

The Ac-225-laden ion exchange medium can be further rinsed with an acid solution such as an about 0.5 to about 10M aqueous nitric or hydrochloric acid solution, preferably about 2.0M to about 3.0M nitric acid, to remove any residual cations of radium isotopes and cations of Ac-225 decay products from the ion exchange medium.

In a present process, the second exchange medium (ion exchange medium) contains diphosphonic acid (DPA) ligands or groups. Several types of DPA containing substituted diphosphonic acids are known in the art and can be used herein. An exemplary diphosphonic acid ligand has the formula $CR^1R^2 (PO_3R_2)_2$, wherein R is selected from the group consisting of hydrogen, a $C_1$–$C_8$ alkyl group, a cation, and mixtures thereof;

$R^1$ is hydrogen or a $C_1$–$C_2$ alkyl group; and $R^2$ is hydrogen or a bond to a polymeric resin. When $R^2$ is a bond to a polymeric resin, the phosphorus-containing groups are present at 1.0 to about 10 mmol/g dry weight of the copolymer and the mmol/g values are based on the polymer where $R^1$ is hydrogen. Exemplary exchange media containing diphosphonic acid ligands are discussed hereinbelow.

One such exchange medium is referred to as Dipex® resin, which is an extraction material containing a liquid diphosphonic acid extractant belonging to a class of diesterified methanediphosphonic acids, such as di-2-ethylhexyl methanediphosphonic acid. The extractant is sorbed on a substrate that is inert to the mobile phase such as Amberchrome™ CG-71 (available from TosoHaas, Montgomeryville, Pa.) or hydrophobic silica. In this extractant, $R^1$ and $R^2$ are H and one R is 2-ethylhexyl and the other is H.

Dipex® resin has been shown to have a high affinity for various tri-, tetra-, and hexa- valent actinides and lanthanides, such as cations of Ac-225, and to have a lower affinity for cations of radium and the decay products of Ac-225. This has been shown even in the presence of complexing anions such as floride, oxalate, and phosphate.

The active component of a preferred Dipex® resin is a liquid diphosphonic acid of the general formula,

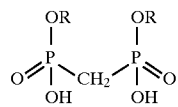

where R is $C_6$–$C_{18}$ alkyl or aryl. A preferred compound is bis-2-ethylhexyl methanediphosphonic acid.

The active component DPA can be mixed with a lower boiling organic solvent such as methanol, ethanol, acetone, diethyl ether, methyl ethyl ketones, hexanes, or toluene and coated onto an inert support, such as glass beads, polypropylene beads, polyester beads or silica gel as known in the art for use in a chromatographic column. Acrylic and polyaromatic resins such as AMBERLITE®, commercially available from Rohm and Haas Company of Philadelphia, Pa., may also be used. In the alternative, a liquid-liquid extraction method can be used, if the diphosphonic acid is dissolved in an organic solvent such as xylene, kerosene, or higher alcohols ($C_5$–$C_{10}$). Higher boiling aromatic solvents such as diethyl benzene, diisopropyl benzene and t-butyl benzene can also be used.

The properties and characteristics of Dipex® resin are more fully described in allowed U.S. patent application Ser. No. 08/467,402, filed Jun. 6, 1995, the disclosure of which is incorporated herein by reference. Dipex® resin is available from Eichrom Industries, Inc.

Another useful resin is Diphosil™ resin. Diphosil™ resin is an ion exchange resin. Similar to the other DPA resins, Diphosil™ resin contains a plurality of geminally substituted diphosphonic acid ligands such as those provided by vinylidene diphosphonic acid. The ligands are chemically bonded to a an organic matrix that is grafted to silica particles. Diphosil™ resin is available from Eichrom Industries, Inc.

Still another resin is Diphonix® resin, which is a particulate ion exchange resin having geminally substituted vinylidene diphosphonic acid (VDPA) ligands chemically bonded to a styrene-divinylbenzene matrix. Diphonix® resin is also available from Eichrom Industries, Inc.

Diphonix® resin particles are prepared by the copolymerization of four groups of monomers. Vinylidene diphosphonic acid or the alkyl or aryl esters thereof constitute one monomer group. The second monomer group comprises acrylamide or styrene, whereas the third group comprises acrylonitrile, methyl acrylate and methyl methacrylate. The fourth group comprises a divinylic or trivinylic cross-linking agent such as divinylbenzene, trimethylolpropane trimethacrylate, trivinylbenzene, diethyleneglycol diacrylate and N,N'-methylene-bis-acrylamide. Divinylbenzene often contains ethyl vinyl benzene as an impurity whose presence does not impair the efficacy of the particles.

Thus, a tetrapolymer is prepared by copolymerizing one monomer from each of the above four monomer groups. The diphosphonate-containing monomer is usually copolymerized as a tetraalkyl or tetraaryl ester whose ester groups are hydrolyzed off after completion of the reaction. A preferred synthesis for this monomer is disclosed in U.S. Pat. No. 5,256,808, whose disclosure is incorporated by reference.

Styrene is a particularly preferred monomer of the second group and acrylonitrile is a particularly preferred monomer of the third group. When styrene is a copolymerized monomer, it is particularly preferred to sulfonate the copolymer particle beads (particles) to provide a copolymer having pendent phenylsulfonate groups. Any sulfonating agent can be used. Use of chlorosulfonic acid as sulfonating agent with a one hour reaction time at room temperature provides complete sulfonation of the phenyl rings. Subsequent hydrolysis with sodium hydroxide converts the chlorosulfonic acid groups to the desired sulfonate groups. Such sulfonation provides particles with enhanced hydrophilicity and microporosity and also typically hydrolyzes some pendent nitrile and ester groups to form pendent carboxylate groups, as well as hydrolyzing the diphosphonate tetraalkyl esters.

The characteristics and properties of Diphonix® resin are more fully described in U.S. Pat. Nos. 5,539,003, 5,449,462 and 5,281,631, whose disclosures are incorporated herein by reference.

Yet another useful resin has pendent —$CR^1(PO_3R_2)_2$ groups added to a preformed water-insoluble copolymer by grafting; i.e., the pendent phosphonate groups are added after copolymer particle formation. For these polymers, R is hydrogen, a $C_1$–$C_8$ alkyl group, a cation or mixtures thereof, and $R^1$ is hydrogen or a $C_1$–$C_8$ alkyl group. A contemplated pendent —$CR^1(PO_3R_2)_2$ group for this group of resins has the formula shown below. The particles also contains zero to about 5 mmol/g dry weight of pendent aromatic sulfonate groups.

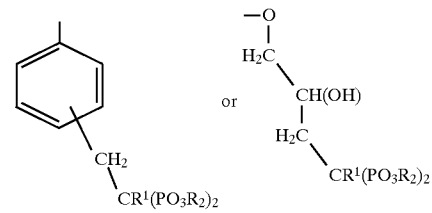

A contemplated pendent methylene diphosphonate as first formed typically contains two $C_1$–$C_8$ dialkyl phosphonate ester groups. Exemplary $C_1$–$C_8$ alkyl groups of those esters and other $C_1$–$C_8$ alkyl groups noted herein include methyl, ethyl, propyl, isopropyl, butyl, t-butyl, pentyl, cyclopentyl, hexyl, cyclohexyl, 4-methylcyclopentyl, heptyl, octyl, cyclooctyl, 3-ethylcyclohexyl and the like, as are well-known. An isopropyl group is a preferred R group. An $R^1$ $C_1$–$C_2$ alkyl group is a methyl or ethyl group, and $R^1$ is most preferably hydrogen.

After formation, the alkyl ester groups are hydrolyzed so that for use, R in the above formula is hydrogen (a proton), $Ca^{+2}$ ion or an alkali metal ion such as lithium, sodium and potassium ions.

As is the case of ion exchange resins generally, an R cation of a contemplated ion exchange resin can be changed at will from a first cation (including a proton) to a second cation by simply washing an aqueous composition of a resin first cation salt with an aqueous solution having an excess of the second cation. These procedures are well-known and need not be discussed further.

The reacted monomers of a contemplated copolymer are quite varied. Exemplary reacted monomers are styrene, ethyl styrene, vinyltoluene, vinylxylene, acrylonitrile, a $C_1$–$C_8$ alkyl acrylate or methacrylate, a vinyl $C_1$–$C_8$ acyl ester, vinylchloride, a $C_1$–$C_8$ alkyl vinyl ether, a vinyl benzylhalide such as α-bromo- or α-fluoromethyl styrene and glycidyl acrylate or methacrylate.

A contemplated $C_1$–$C_8$ acyl group is an acyl form of one of the above $C_1$–$C_8$ alkyl groups, as appropriate. Some $C_1$–$C_8$ alkyl groups such as cyclohexyl and t-butyl do not have corresponding acyl groups, as is well-known.

A contemplated insoluble copolymer contains at least 1.0 mmol/g dry polymer weight and preferably about 2.0 mmol/g of a reacted (copolymerized) vinylbenzyl halide or glycidyl acrylate or methacrylate or both so that the above amount of pendent phosphonate groups can be prepared. In addition, where a pendent aromatic sulfonate is present as is preferred, an appropriate amount of reacted aromatic monomer such as styrene, vinyl toluene or the like must also be present.

Preferably, the insoluble copolymer contains at least 2 mole percent reacted vinylbenzyl halide or glycidyl acrylate or methacrylate, with that percentage more preferably being about 10 to about 95 mole percent. One or more reacted monoethylenically unsaturated monomers as discussed before are present at about 2 to about 85 mole percent, with this monomer preferably including at least 5 mole percent of an above monoethylenically unsaturated aromatic monomer such as styrene, ethyl styrene, vinyl toluene (methyl styrene) and vinyl xylene.

A useful insoluble copolymer also includes a reacted cross-linking agent (cross-linker). Reacted cross-linking agents useful herein are also quite varied. Exemplary cross-linking agents useful herein are selected from the group consisting of divinylbenzene, trimethylolpropane triacrylate or trimethacrylate, erythritol tetraacrylate or tetramethacrylate, 3,4-dihydroxy-1,5-hexadiene and 2,4-dimethyl-1,5-hexadiene. Divinylbenzene is particularly preferred here.

The amount of reacted cross-linker is that amount sufficient to achieve the desired insolubility. Typically, at least 0.3 mole percent reacted cross-linker is present. The reacted cross-linking agent is preferably present at about 2 to about 20 mole percent.

These contemplated particles are the multi-step reaction product of a nucleophilic agent such as $CR^1(PO_3R_2)_2^-$, which can be obtained by known methods, with a substrate. Thus, $CHR^1(PO_3R_2)_2$, where R is preferably an alkyl group, is first reacted with sodium or potassium metal, sodium hydride or organolithium compounds, e g., butyllithium, or any agent capable of generating a diphosphonate carbanion. The resulting carbanion is then reacted with a substrate that is a before-discussed insoluble cross-linked copolymer of one or more of vinyl aliphatic, acrylic, or aromatic compounds and a polyvinyl aliphatic, acrylic, or aromatic compound, e.g., divinylbenzene. That copolymer contains at least 2 mole percent of a reacted halogenated derivative of vinyl aromatic hydrocarbon such as vinylbenzyl chloride, or glycidyl ester group, preferably from 10 to 95 mole percent, about 2 to about 85 mole percent of monovinyl aromatic hydrocarbon such as styrene and at least 0.3 mole percent of polyvinyl aliphatic and/or aromatic cross-linker such as divinylbenzene, preferably 2–20 mole percent.

A suitable insoluble, cross-linked copolymer can be obtained by any well-known method used in styrene or acrylate polymerization (e.g., suspension and emulsion polymerization) but the suspension method is preferred because the insoluble copolymer is formed as beads suitable for column separation processes and the diameter of the beads can be easily controlled. Such polymerization can be performed in the presence of no solvent; i.e., neat or without diluent as a bulk polymerization, to about 90 weight percent of inert solvent or diluent such as alcohols, aliphatic and aromatic hydrocarbons or any of their mixtures. The vinyl aromatic compounds can contain lower alkyl groups with 1 to 3 carbon atoms in addition to the vinyl group. Examples of such monomers are vinyltoluene and vinylxylene.

The next step in preparing contemplated particles is the substitution of a methylene diphosphonate group for the halogen atom in the halomethyl groups on the aromatic units (e.g., vinylbenzyl chloride) or, for example, the epoxide group in glycidyl acrylate or methacrylate. The copolymer containing such units is reacted with the carbanion $CR^1(PO_3R_2)_2^-$. Halogen is thereby displaced from the halomethyl groups or epoxy groups are opened, and a polymeric resin containing pendent methylene diphosphonate groups is formed.

The reaction of tetraalkyl methylene diphosphonate (after it is converted into a carbanion with sodium or potassium metal, sodium hydride, butyllithium, etc.) with insoluble, cross-linked copolymer containing halomethyl, ester, or epoxy groups to graft the phosphorous-containing pendent groups can be carried out at temperatures between about −25° and about 250° C., preferably from about 100° to about 170° C. The reaction is preferably carried out while the copolymer is swollen by an organic solvent such as toluene, xylenes, ethylbenzene or mesitylene.

Thus, the reaction is preferably carried out by swelling a before-discussed insoluble cross-linked polymer in one of the aforementioned solvents for 0.1–2 hours at a temperature from ambient to the boiling point of the solvent, and subsequent addition of a 1- to 5-fold excess of tetraalkyl methylene diphosphonate carbanion in a small amount of the same solvent. Reaction is usually carried out by refluxing a mixture at atmospheric pressure for one to 48 hours, preferably 10 to 24 hours.

The grafted copolymer product so prepared is recovered by separation from the liquid by filtering, centrifugation, decantation and the like. The grafted copolymer can be washed with organic solvents such as benzene, toluene or ethylbenzene to free the product of unreacted tetraalkyl methylene diphosphonate and dried.

The copolymer containing grafted methylene diphosphonate tetraalkyl ester groups in an amount corresponding to about 1.0 mmol/g of dry weight, preferably from 2 to 7 mmol/g of dry weight, is preferably reacted with a sulfonating agent such as chlorosulfonic acid, concentrated sulfuric acid or sulfur trioxide in order to introduce strongly acidic pendent aromatic sulfonic groups (shown below in pertinent part as before) into their structure. The presence of the sulfonate pendent groups confers the additional advantage of hydrophilicity to the particles and leads to a surprising enhancement in the rate of cation complexation without adversely affecting the observed selectivity.

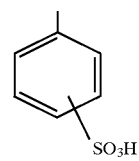

The reaction of the sulfonating agent with a grafted copolymer containing methylene diphosphonate groups is usually carried out when the recovered resin product in ester form is swollen by a halohydrocarbon such as dichloromethane, ethylene dichloride, chloroform and 1,1,1-trichloroethane. The sulfonation reaction can be performed using 0.5 to 20.0 weight percent of chlorosulfonic acid in one of the mentioned halohydrocarbon solvent at temperatures ranging from about −25° to about 50° C., preferably at about 10° to about 30° C. The reaction is carried out by contacting resin preswollen for zero (unswollen) to about two hours with the above sulfation solution for 0.25 to 20 hours, preferably 0.5 to two hours.

After completion of the sulfonation reaction, the particles are separated from the liquid reaction medium by filtration, centrifugation, decantation, or the like. This final, second resin product is carefully washed with dioxane, water, 1M NaOH, water, 1M HCl and water, and then dried.

The sulfonation reaction and work-up in water also hydrolyzes the phosphonate $C_1$–$C_8$ alkyl ester groups. Where sulfonation is not carried out, hydrolysis of the phosphonate esters can be carried out by reaction with an acid such as concentrated hydrochloric acid at reflux.

These contemplated particles contain as pendent functional groups both methylene diphosphonate and sulfonate groups, directly attached to carbon atoms of aromatic units or acrylate or methacrylate units in the polymer matrix. A contemplated resin displays high affinity towards a wide range of divalent, trivalent and multivalent cations over a wide range of pH values. At a pH value below 1, the resins are able to switch from an ion-exchange mechanism of cation removal to a bifunctional ion-exchange/coordination mechanism due to the coordination ability of the phosphoryl oxygens. The sulfonic acid groups then act to make the matrix more hydrophilic for rapid metal ion access; the methylene diphosphonate groups are thus responsible for the high selectivity.

A contemplated precursor insoluble copolymer can be prepared neat, in the absence of solvent or diluent by bulk polymerization techniques, or in the presence of a solvent or dispersing agent. A liquid solvent/dispersant is preferred here for use in a suspension polymerization so that the copolymer is prepared in the form of particles having a generally spherical shape; i.e., as beads, and a substantially narrow size distribution. Copolymer produced by bulk polymerization is typically broken to particles of irregular shape and a wide size distribution.

A contemplated copolymer and completed particle can have a size such that the particles pass through a sieve having a 4 millimeter (mm) opening and are retained on a sieve having an opening of about 0.004 mm. Particles that are sized to pass through a sieve screen with an opening of about 0.15 mm and be retained on a mesh of 0.004 mm are particularly useful for chromatographic separations. Larger sized particles are particularly useful for ion separations wherein the resin particles are filtered to effect a physical separation of one complexed polyvalent metal ion from one or more other mono- or polyvalent metal ions.

The preparation of ion-exchange/coordination particles containing both methylene diphosphonate and sulfonate groups on insoluble, cross-linked copolymers as herein described permits the production of materials having enhanced selectivity and improved kinetics of cation removal, especially in a low pH value range, than it has heretofore been obtained by the introduction of methylene diphosphonate or sulfonate groups alone.

Still further useful DPA copolymer resin particles are copolymers described in Sundell et al., *Chem. Mater.*, 5:372–376 (1993) and Sundell et al., *Polym. Prep.*, 33:992 (1992) that are said to be useful as catalyst supports. These are terpolymers prepared by copolymerizing styrene, 1-(vinylphenyl)propane-2,2-bis(phosphonic acid) and divinylbenzene. In one reported synthesis, a microemulsion was prepared by the addition of water (0.26 g) to a styrene (23.52 mmol)/divinylbenzene (15.71 mmol) mixture containing bis(2-ethylhexyl)sulfosuccinate sodium salt (0.675 g). The above 1-(vinylphenyl)propane-2,2-bis(phosphonic acid) (1.4 mmol) was added portionwise to the microemulsion. The microemulsion was maintained at 30° C. until optically clear. Azobisisobutyronitrile (24 mg) was added, the reaction vessel was closed and polymerization was initiated by heating to a temperature of 60° C. for 12 hours. The resulting porous copolymer was then ground to form particles.

Figure 4:
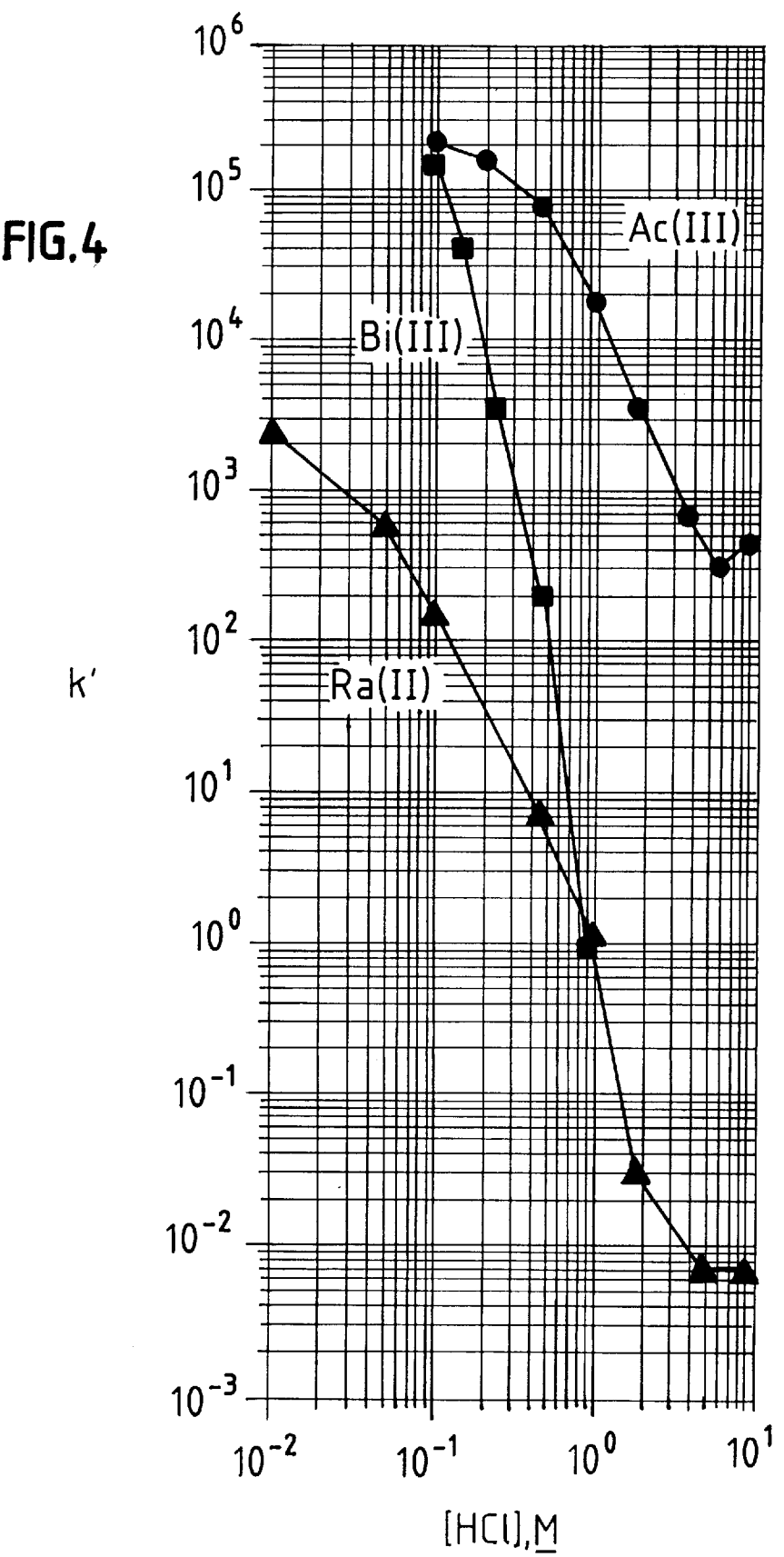
FIG. 4 is a graphic illustration of the uptake of actinium III (circles), bismuth II (squares) and radium II (triangles) cations by Dipex® exchange medium (extraction resin) measured as in FIG. 3 relative to the concentration of the hydrochloric acid carrier solution.
Figure 5:
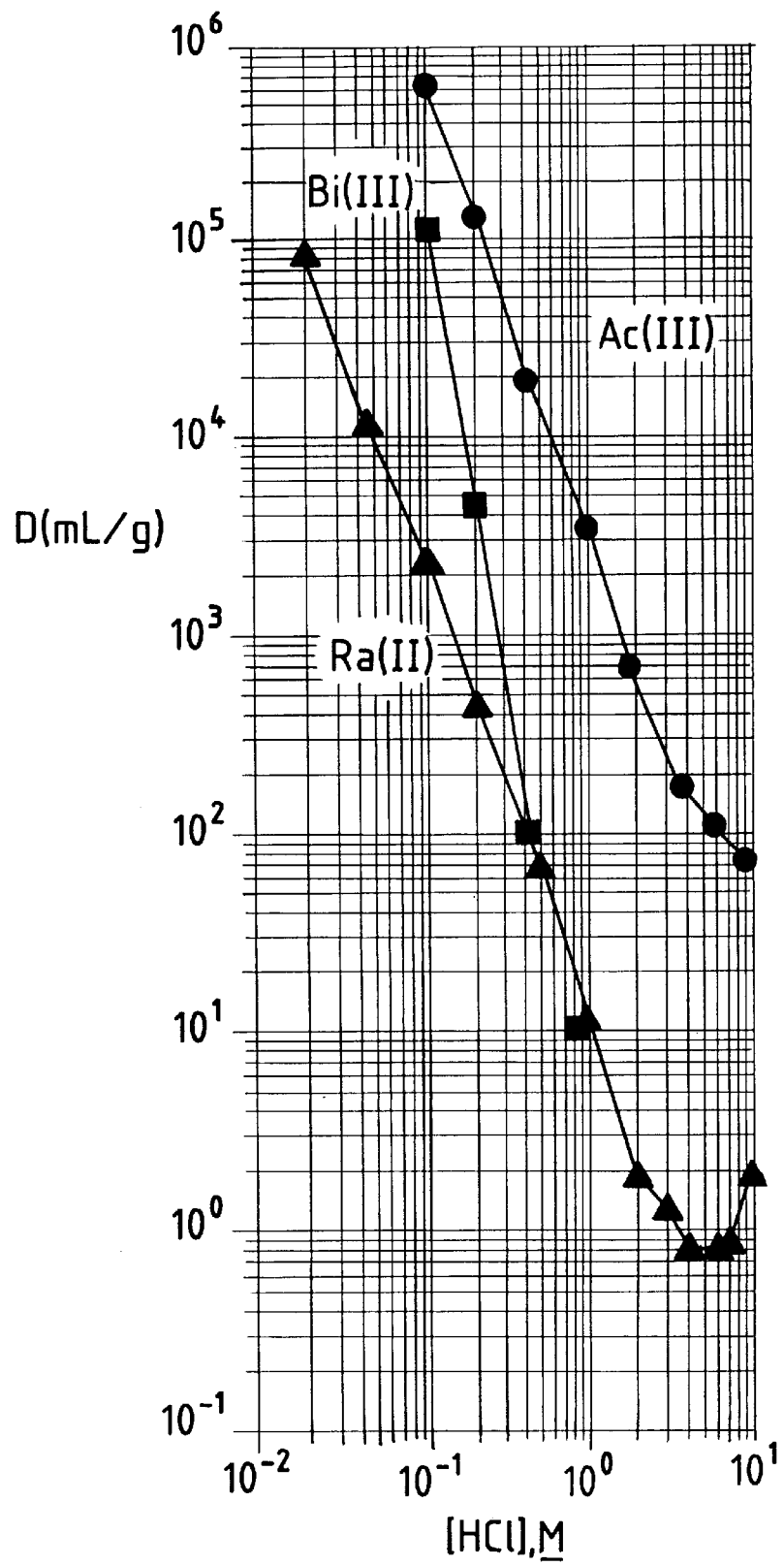
FIG. 5 is a graphic illustration of the uptake of actinium, bismuth and radium cations as in FIG. 4 by Diphonix® ion exchange resin (exchange medium) measured as distribution values (D) relative to the concentration of the hydrochloric acid carrier solution.

FIGS. 4 and 5 graphically illustrate the uptake of selected cations by the Dipex® and Diphonix® resins, respectively, in varying concentrations of hydrochloric acid.

The Ac-225-laden ion exchange medium is typically isolated in a vessel, such as an ion exchange column, that has been accordingly fitted with elements, such as plates and the like, to promote intimate contact between the solutions and the ion exchange resin.

Prior to "growing" the Bi-213, which is carried out in the column, the Ac-225-laden ion exchange medium is rinsed with about 0.5 to about 10M, and preferably about 2.0 to about 3M, nitric acid followed by extensive rinsing with about 0.05 to about 10M, and preferably 2.0 to about 3M, hydrochloric acid. The hydrochloric acid solution rinse further decontaminates the Ac-225 in the medium by displacing the nitric acid in the column. Any radium that may have been retained in the column is rinsed away with the hydrochloric acid rinse. With the removal of any traces of radium, the Ac-225 is fully separated from the radium and the possibility of growing Bi-212 (which undesirably produces the radioactive gas Rn-220 during decay) is greatly reduced or eliminated.

The Ac-225-laden ion exchange medium, loaded in the column, is maintained for a predetermined period of time so that the Ac-225 incubates on the column to "grow" Bi-213 cations. This type of "maintenance" is referred to in the art as "growing" a desired nuclide. In a preferred process, the Ac-225 is maintained for a period of about 3 hours to about 4 hours, until the Bi-213 approaches equilibrium. The Bi-213 is then eluted from the column using an acid eluting solution.

Elution can be with about 0.5 to about 10M aqueous acid. In a preferred process, the Bi-213 is eluted using a hydrochloric acid solution having a concentration of about 0.7M so that on neutralization with NaOH, a physiologically appropriate saline solution results.

As will be discussed more fully herein, the column, loaded with the Ac-225-laden ion exchange medium, constitutes a "stand-alone", transportable unit from which Bi-213 can be eluted for patient administration. The column can be transported to a patient's room for bed-side radiotherapy treatment, with the Bi-213 eluted directly from the column and prepared locally for patient administration.

It is contemplated that the eluted acidic Bi-213 solution be neutralized with an appropriate, medically acceptable base, such a sodium hydroxide, and diluted to form an isotonic solution for patient administration. The Bi-213 cation solution can be assayed prior to neutralization and dilution.

Advantageously, the thorium-laden TEVA™ resin (the thorium-laden first exchange medium) can be regenerated after it is used to remove the thorium isotopes from the feed solution. It has been found that the thorium can be eluted from the thorium-laden TEVA™ resin by contacting the resin with about 0.01 to about 10M, and preferably about 1.0M, hydrochloric acid followed by a nitric acid rinse. The resultant thorium fraction can be evaporated to dryness and converted back to nitrate salt by heating in 2.0M nitric acid and again evaporating the resultant liquid to dryness. The thorium fraction can be reused by reloading the thorium onto the TEVA™ resin column or onto a subsequent exchange column.

Optionally, in-line filters having some exchange capability can be positioned at various locations within the process. In a current process, an in-line filter having a quantity of exchange resin, such as bis-2-ethylhexyl phosphoric acid (HDEHP) resin, is positioned between the TEVA™ and DPA medium-containing columns to filter out solids that may have carried over from the TEVA™ resin column, and to remove any traces of Th-228 and Th-229 that may have passed through the TEVA™ resin column as a result of, for example, channelling through the column. Unlike the TEVA™ resin column, the HDEHP resin cannot be regenerated and is therefore disposed of as waste when it has become exhausted.

An in-line filter can also be positioned after the DPA resin column, prior to the patient administration apparatus (not shown). The filter serves to remove solid matter in the liquid stream prior to preparation for, and patient administration. The filter can also include a quantity of ion exchange media, such as Diphosil™ or Diphonix® resin to capture any Ac-225 that may breakthrough the DPA resin column.

Figure 6:
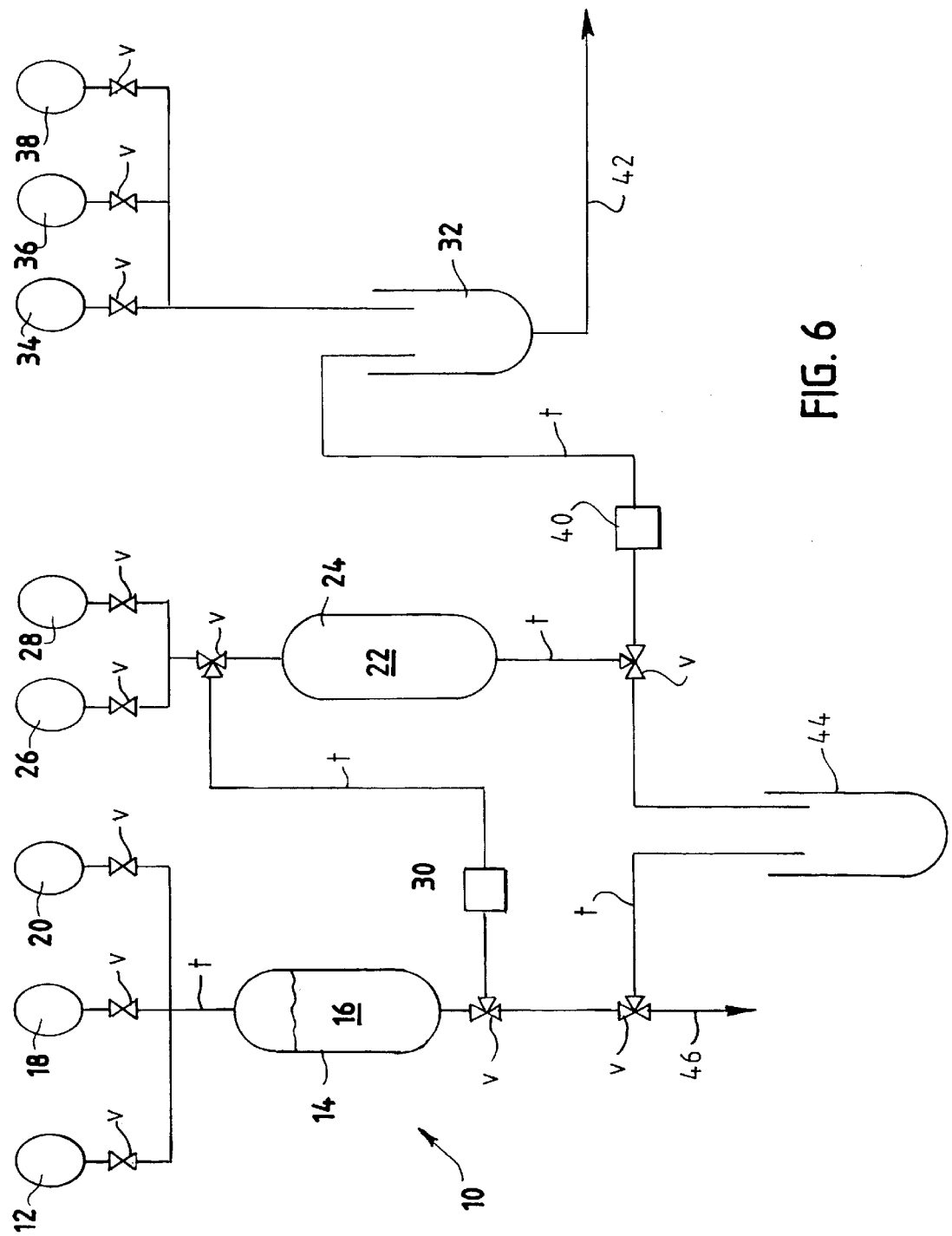
FIG. 6 is a schematic arrangement of an exemplary system for producing the substantially impurity-free Bi-213 in accordance with the principles of the present invention.

A schematic arrangement of an apparatus or system 10 that is used to carry out the present process is illustrated in FIG. 6. The apparatus 10 is provided with a starting material 12 having Th-229. As discussed above, the starting material can contain other radio-isotopes, such as Th-228 and the decay products of Th-228 and Th-229. In a current embodiment, the Th-229 is provided by separation of the decay products resulting from the decay of U-233.

In the illustrated embodiment, the starting material 12 is introduced into a vessel or column 14 that is loaded with the TEVA™ resin 16. The starting material 12 is introduced in an acid solution. The column is in flow communication with a pair of acid solution storage sources 18, 20 for feeding, for example, the nitric acid solution and the regeneration solution, e.g., hydrochloric acid solution to the TEVA™ resin column 14.

The TEVA™ resin column 14 is in flow communication with the DPA resin 22 column 24. The DPA resin column 24 includes provisions for introducing other solutions to the column 24 from, for example, a nitric acid solution storage source 26 and a hydrochloric acid solution storage source 28. An in-line filter 30 that can include exchange capabilities, such as the HDEHP resin in-line filter 30, can be positioned between the discharge of the TEVA™ resin column 14 and the inlet of the DPA resin column 24.

Flow communication is provided between the various components of the system 10 by tubing t, such as flexible Tygon® tubing, with the tubing sections t interconnected by quick disconnect-type fittings, such as Luer lock fittings (not shown). Likewise, quick-disconnect fittings are used to connect the tubing sections t to the various system 10 components. Valves v are positioned in the system 10 to direct the fluid to the desired system 10 components. It is desirable that the valves v be remotely operable, such as by solenoid operators, to reduce radiation exposure to operating personnel.

As provided previously, the DPA resin column 24 is a stand-alone unit that can be separated from the other components of the system 10 and transported to, for example, a patient's bed-side or the immediate vicinity of the bed-side for local radiotherapy administration. It is contemplated that the DPA resin column 24 is appropriately shielded to reduce radiation exposure to personnel during handling, to reduce the radiation exposure to the patient during administration and to reduce the overall ambient radiation levels due to the radionuclides present in the system 10.

The eluted Bi-213 solution can be retained in, for example, a mixing chamber 32, so that the solution can be neutralized and diluted to form an isotonic solution prior to patient administration. The mixing and neutralization chamber 32 can include provisions for adding various solutions to the chamber 32, such as from a sodium hydroxide (base) storage source 34, and a deionized water storage source 36. It is also contemplated that a source for a sterilizing agent 38, such an alcohol, is provided. All of the mixing chamber 32 inputs accordingly include valves v for initiating and terminating flow of the appropriate solutions thereto.

An in-line filter 40 can be provided in the system 10, in the tubing t between the DPA resin column 24 and the mixing chamber 32. As provided previously, the in-line filter 40 can include some ion exchange capability form, for example, a quantity of an ion exchange medium such as Diphosil™ or Diphonix® resin. An outlet line 42 extends from the mixing chamber 32 for providing the Bi-213 solution for patient administration.

The system 10 can include a waste receptacle 44 that is used to collect waste products from the process. The waste products from the receptacle 44 will be disposed of in accordance with good practices, which good practices will be understood by those skilled in the art.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A process for producing substantially impurity-free Bi-213 cations comprising the steps of:
    (a) contacting an acidic feed solution containing Ac-225 cations with an ion exchange medium having a plurality of binding sites thereon adapted to bind said Ac-225 thereto to form an Ac-225-laden ion exchange medium;
    (b) maintaining said Ac-225-laden ion exchange medium for a predetermined period of time so as to form Bi-213 cations from Ac-225 by radioactive decay;
    (c) contacting an acid solution with said Ac-225-laden ion exchange medium to release said Bi-213 therefrom, to form a Bi-213 cations acid solution; and
    (d) recovering said Bi-213 acid solution from said Ac-225-laden ion exchange medium to form a substantially impurity-free Bi-213 acid solution.

2. The process for producing substantially impurity-free Bi-213 cations in accordance with claim 1 wherein said acidic feed solution is prepared by further steps that comprise contacting an acidic solution containing thorium, radium and actinium cations with an exchange medium having a plurality of binding sites thereon adapted to bind said thorium to form a thorium-laden exchange medium, and to remove said thorium to form said acid feed solution that contains actinium and radium cations (a Ra/Ac solution).

3. A process for producing substantially impurity-free Bi-213 cations comprising the steps of:
    (a) contacting an about 1 to about 10M nitric acid solution containing thorium, radium and actinium cations with a first exchange medium having a plurality of binding sites thereon adapted to bind said thorium to form a thorium-laden exchange medium, and to remove said thorium to form an acidic Ra/Ac solution that contains actinium and radium cations in which said actinium is present as Ac-225;

(b) contacting said Ra/Ac solution containing Ac-225 cations with a second ion exchange medium having a plurality of binding sites thereon adapted to bind said Ac-225 thereto to form an Ac-225-laden ion exchange medium;

(c) maintaining said Ac-225-laden ion exchange medium for a predetermined period of time so as to form Bi-213 cations from Ac-225 by radioactive decay;

(d) contacting an acid solution with said Ac-225-laden ion exchange medium to release said Bi-213 therefrom, to form a Bi-213 cations acid solution; and (e) recovering said Bi-213 acid solution from said Ac-225-laden ion exchange medium to form a substantially impurity-free Bi-213 acid solution.

4. The process for producing substantially impurity-free Bi-213 cations in accordance with claim 3 including the step of contacting said Ra/Ac solution with a second quantity of said first exchange medium having a plurality of binding sites thereon adapted to bind thorium thereto prior to step (b).

5. The process for producing substantially impurity-free Bi-213 cations in accordance with claim 3 including rinsing said thorium-laden exchange medium with an aqueous nitric acid solution having a concentration of about 1.0M to about 10.0M nitric acid to remove residual radium and Ac-225 therefrom, and combining said extracted radium and Ac-225 with said Ra/Ac solution to form a combined aqueous Ra/Ac solution.

6. The process for producing substantially impurity-free Bi-213 cations in accordance with claim 3 including contacting said thorium-laden exchange medium with an aqueous hydrochloric acid solution having a concentration of about 0.01 to about 10M to extract said thorium and form a solution of thorium cations in said aqueous hydrochloric acid.

7. The process for producing substantially impurity-free Bi-213 cations in accordance with claim 3 including the step of further contacting the substantially impurity-free Bi-213 cation acid solution with a second quantity of a second exchange resin having a plurality of binding sites thereon adapted to bind Ac-225 cations thereto prior to step (e).

8. The process for producing substantially impurity-free Bi-213 cations in accordance with claim 3 wherein said acidic feed solution is aqueous nitric acid in which the nitric acid concentration is about 2.0M to about 3.0M.

9. The process for producing substantially impurity-free Bi-213 cations in accordance with claim 3 including contacting said Ac-225-laden ion exchange medium with an aqueous solution of about 0.5 to about 10M nitric acid or hydrochloric acid to remove cations of radium isotopes and cations of Ac-225 decay products therefrom.

10. The process for producing substantially impurity-free Bi-213 cations in accordance with claim 9 wherein the acid solution of step (d) is an aqueous hydrochloric acid solution having a hydrochloric acid concentration of about 0.7M.

11. An apparatus for producing substantially impurity-free Bi-213 cations from a starting material of thorium, comprising:

a first exchange medium having a plurality of binding sites thereon, said binding sites having an affinity for binding thorium cations thereto and having a lower affinity for binding radium cations and Ac-225 cations thereto;

a first acid supply in flow communication with said exchange medium, said first acid supply adapted to supply a first aqueous acid to carry said starting material to said exchange medium;

a first vessel adapted to retain said first exchange medium and further adapted to maintain contact between said exchange medium and said first aqueous acid;

a second vessel in flow communication with said first vessel and adapted to retain therein a second exchange medium having a plurality of binding sites thereon that have an affinity for binding Ac-225 cations thereto and having a lower affinity for binding radium cations and other cations of +2 and +1 valency thereto;

a second aqueous acid supply in flow communication with said second vessel and adapted to supply a second acid to said second vessel, said second vessel being separable from said first vessel; and a third aqueous acid supply in flow communication with said second vessel.

12. The apparatus for producing substantially impurity-free Bi-213 cations in accordance with claim 10 including at least one in-line filter.

13. The apparatus for producing substantially impurity-free Bi-213 cations in accordance with claim 11 wherein said at least one in line filter includes an exchange medium.

14. The apparatus for producing substantially impurity-free Bi-213 cations in accordance with claim 11 wherein said at least one in-line filter is positioned between said first and second vessels.

* * * * *